US012440254B2

(12) United States Patent
Yamamoto

(10) Patent No.: US 12,440,254 B2
(45) Date of Patent: Oct. 14, 2025

(54) SURGICAL METHOD FOR CHANGING A NASOLABIAL ANGLE

(71) Applicant: Koji Yamamoto, Aichi (JP)

(72) Inventor: Koji Yamamoto, Aichi (JP)

( * ) Notice: Subject to any disclaimer, the term of this patent is extended or adjusted under 35 U.S.C. 154(b) by 630 days.

(21) Appl. No.: 17/973,626

(22) Filed: Oct. 26, 2022

(65) Prior Publication Data

US 2023/0240733 A1 Aug. 3, 2023

Related U.S. Application Data

(60) Provisional application No. 63/305,437, filed on Feb. 1, 2022.

(51) Int. Cl.

| | |
|---|---|
| ***A61B 17/80*** | (2006.01) |
| ***A61B 17/56*** | (2006.01) |
| ***A61B 34/10*** | (2016.01) |
| ***A61B 90/00*** | (2016.01) |

(52) U.S. Cl.

CPC .......... *A61B 17/8071* (2013.01); *A61B 34/10* (2016.02); *A61B 2017/564* (2013.01); *A61B 2017/568* (2013.01); *A61B 2034/105* (2016.02); *A61B 2034/108* (2016.02); *A61B 2090/3762* (2016.02)

(58) Field of Classification Search

CPC ................ A61B 17/8071; A61B 34/10; A61B 2034/105; A61B 2090/3762; A61B 2017/564; A61B 2017/568

See application file for complete search history.

(56) References Cited

FOREIGN PATENT DOCUMENTS

| | | | | | |
|---|---|---|---|---|---|
| CN | 111281603 A | * | 6/2020 | ............. | A61F 2/186 |
| CN | 112022235 A | * | 12/2020 | ............. | A61F 2/186 |
| WO | WO-2021085903 A1 | * | 5/2021 | ............. | A61F 2/186 |

* cited by examiner

*Primary Examiner* — Kevin T Truong
*Assistant Examiner* — Diana Jones
(74) *Attorney, Agent, or Firm* — Renner, Otto, Boisselle & Sklar, LLP

(57) ABSTRACT

A surgical method for changing a nasolabial angle of a patient includes the steps of forming a metal implant plate using a jaw bone model of the patient, dissecting a site on the patient for implantation of the metal implant plate, bending the metal implant plate to match a bone surface of the patient at the site, and fixing the metal implant plate to the bone surface.

12 Claims, 6 Drawing Sheets

SURGICAL METHOD FOR CHANGING A NASOLABIAL ANGLE

TECHNICAL FIELD

The present disclosure relates generally to oral cosmetic surgery, and more particularly to an oral cosmetic surgery for changing a nasolabial angle.

BACKGROUND

Orthodontic treatment among adults is gaining attention, as many patients seeking orthodontic treatment aim to have a highly aesthetic, ideal and transverse face. For example, many patients desire tooth alignment, improvement of mouth protrusion, and an aesthetic smile. In particular, nasal base column prosthesis insertion may be performed to improve the nasolabial angle in cosmetic surgery. However, in addition to the cost and time commitment involved with cosmetic surgery, there are also several risks and complications associated with such cosmetic surgery, such as prosthesis misalignment, risk of infection, difficulty in laughing due to foreign body sensation, and risk of prosthetic bone resorption. However, attempts to improve the E-line and nasolabial angle with orthodontic treatment alone have resulted in excessive tooth movement, which leads to prolonged treatment and burden on teeth, as well as an older appearance of the patient due to decreased tooth exposure.

Methods, such as Le Fort II osteotomy of the jaw bone, prosthesis insertion around the piriform orifice, fat grafting, and hyaluronic acid injection treatment have been considered for improving the appearance of patients with midface retraction. However, satisfactory outcomes are not often achieved with these methods and several postoperative problems are typically reported with regard to these methods. Specifically, Le Fort II osteotomy is used in patients with maxillary deformity presenting with mesofacial recessive growth. This procedure improves the jaw-bite relationship and the sensation of depression around the nose. However, the procedure is limited by its invasive nature. Therefore, another method involving the complete mouth combined with an endoscope was introduced to remove the possibility of leaving postoperative scars on the face. However, the invasiveness of such methods remains a challenge and concern for patients. Less invasive methods, such as silicone implantation and fat grafting, however, are not recommended as silicone implantation for example has been associated with several postoperative bone resorptions, and the injected material used in fat grafting tends to leak to the surroundings as the surgical site moves. Also, there is a risk of blood vessel imperforation by inserting hyaluronic acid.

SUMMARY

An improved method for achieving the desired aesthetics in a patient having a midface depression is described herein. The method includes shifting the soft tissue Sn point forward while preventing the backward movement of the soft tissue. The method uses an implant metal plate to support the periosteum around the hard tissue point A, which is the deepest point on the maxillary external linear line between the anterior nasal spine and the intermaxillary central incisor alveolar process crest. The method described herein is superior to the conventional Le Fort type II and prosthesis insertion methods since it is relatively more affordable, less invasive, and has a lower risk of bone resorption.

According to an aspect of this disclosure, a surgical method for changing a nasolabial angle of a patient includes the steps of forming a metal implant plate using a jaw bone model of the patient. The method also includes dissecting a site on the patient for implantation of the metal implant plate and bending the metal implant plate to match a bone surface of a jaw bone of the patient at the site. The method then includes fixing the metal implant plate to the bone surface to increase the nasolabial angle of the patient.

According to an embodiment of any paragraph(s) of this disclosure, the method further includes a step of applying local anesthesia to the site of the patient before dissecting the site.

According to another embodiment of any paragraph(s) of this disclosure, the method further includes a step of confirming that there is no penetration of the two screws into a nasal cavity of the patient and that there is no contact between the two screws and a root of the metal implant plate.

According to another embodiment of any paragraph(s) of this disclosure, the method further includes a step of suturing the site closed.

According to another embodiment of any paragraph(s) of this disclosure, the step of forming the metal implant plate includes the steps of imaging the jaw bone of the patient, forming the jaw bone model of the patient, and bending the metal implant plate to match a model jaw bone surface of the jaw bone model.

According to another embodiment of any paragraph(s) of this disclosure, the step of imaging the jaw bone of the patient includes imaging with computed tomography (CT) imaging.

According to another embodiment of any paragraph(s) of this disclosure, the step of forming the jaw bone model of the patient includes forming the jaw bone model by three-dimensional printing.

According to another embodiment of any paragraph(s) of this disclosure, the step of dissecting the site includes dissecting a gingiva mucosa of the patient from a gum-buccal junction of a maxilla of the patient.

According to another embodiment of any paragraph(s) of this disclosure, the fixing the metal implant plate to the bone surface includes the steps of cutting the bone surface and embedding two screws into the bone surface.

According to another embodiment of any paragraph(s) of this disclosure, the step of cutting the bone surface includes cutting the bone surface with a drill bur.

According to another embodiment of any paragraph(s) of this disclosure, the two screws each have a diameter of 2.0 mm and a length of 5.0 mm.

According to another embodiment of any paragraph(s) of this disclosure, the step of embedding the two screws into the bone surface includes screwing each of the two screws into the bone surface between a lower edge of a piriform aperture and an anterior teeth of the maxilla of the patient.

The following description and the annexed drawings set forth in detail certain illustrative embodiments described in this disclosure. These embodiments are indicative, however, of but a few of the various ways in which the principles of this disclosure may be employed. Other objects, advantages and novel features will become apparent from the following detailed description when considered in conjunction with the drawings.

BRIEF DESCRIPTION OF DRAWINGS

The annexed drawings show various aspects of the disclosure.

DETAILED DESCRIPTION

Figure 1A:
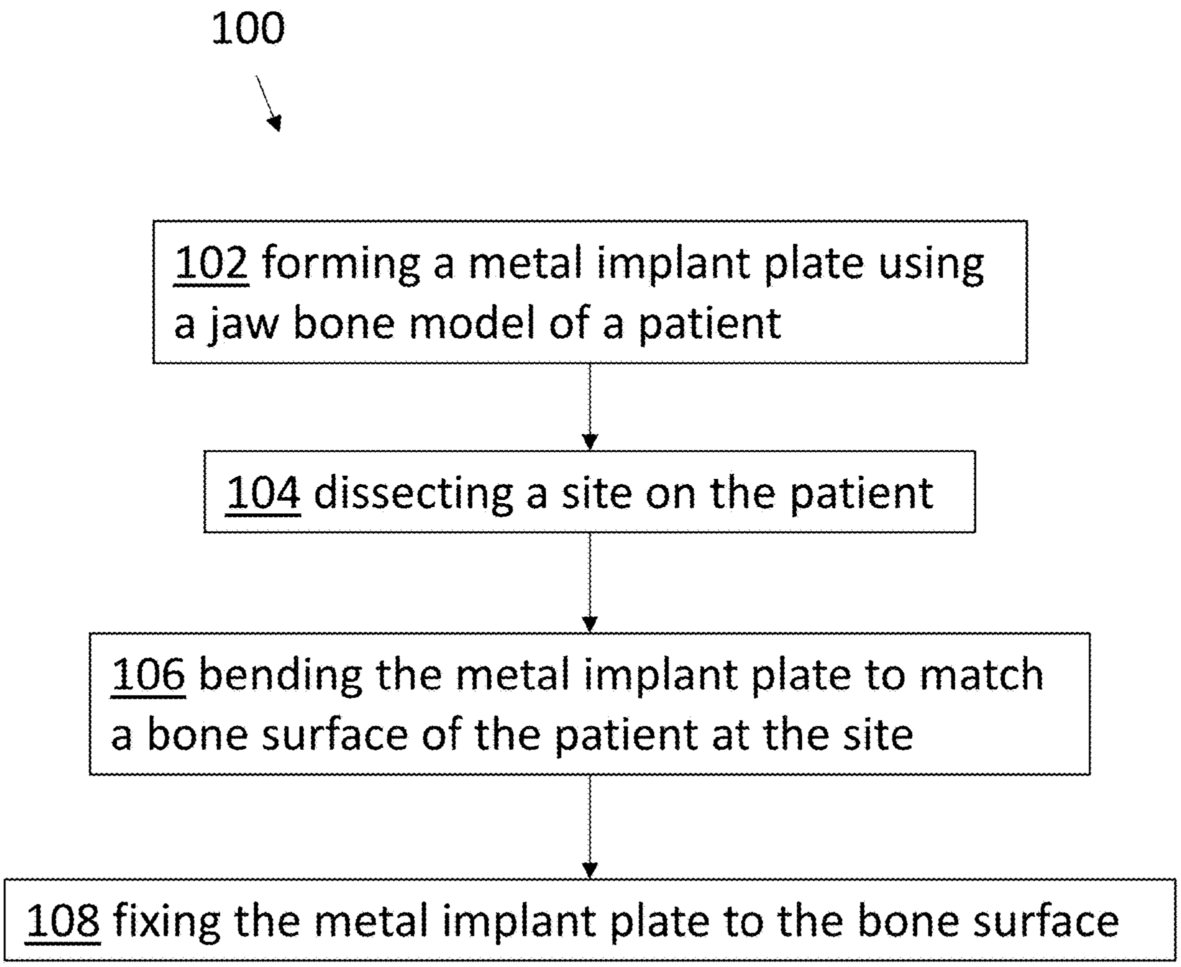
FIG. 1A is a flowchart of a surgical method for changing a nasolabial angle of a patient.
Figure 1B:
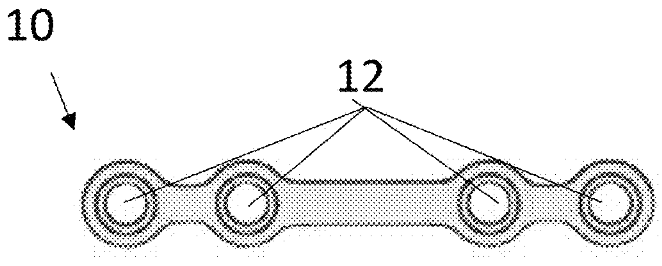
FIG. 1B is a top view of a metal implant plate.

Described herein is a surgical method for changing the nasolabial angle of a patient. With reference to FIG. 1, the method 100 includes a step 102 of preoperatively forming a metal implant plate using a jaw bone model of the patient. The step 102 of forming the metal implant plate may include the steps of imaging the jaw bone of the patient, forming a jaw bone model of the patient, and bending the metal implant plate to match a model jaw bone surface of the jaw bone model. For example, the step of imaging the jaw bone of the patient may include imaging with computed tomography (CT) imaging. However, it is understood that other suitable types of imaging may be used. The step of forming the jaw bone model of the patient may include forming by three-dimensional printing, for example with a three-dimensional printer. However, it is understood that other suitable types of forming may be used. The metal implant plate may be formed with titanium, which has good biocompatibility with the user. A thickness of the metal implant plate may be between 1.0 mm and 3 mm, for strength and durability. For example, the thickness of the metal implant plate may be 1 mm. A length of the metal implant plate may be between 25 mm and 35 mm. For example, the length of the metal implant plate may be 30 mm. A tip of the plate can be bent during surgery to adjust the length of the plate. An embodiment of a metal implant plate 10 according to this disclosure is depicted in FIG. 1B. The plate may include at least two holes 12 for fixing the metal plate to a bone surface of the patient, as will be described in more detail below.

The method 100 may then include a step of applying local anesthesia to a site on the patient for implantation of the metal plate. The local anesthesia may be, for example, Aura Injection Dental Cartridge (Showa Pharmaceutical Co., Ltd. Aichi, Japan), and may include 1.8 mL per dose. Other types of suitable anesthesia include Citanest, Xylocaine and the like. The method 100 then includes a step 104 of dissecting the site on the patient for implantation of the metal implant plate. The site on the patient may be near the gum-buccal junction of the maxilla of the patient. Therefore, the step 104 of dissecting may include dissecting a gingiva mucosa of the patient from a left and a right side of the gum-buccal junction of the maxilla. The step 104 of dissecting may be performed using, for example, a blade no. 12 or a blade no. 15. The method 100 then includes a step 106 of bending the metal implant plate to match a bone surface of the patient at the site, and a step 108 of fixing the metal implant plate to the bone surface. For example, the step of fixing the metal implant plate may include screwing the metal implant plate into the bone surface with two screws. Specifically, the screws may be screwed into the bone surface between the lower edge of the piriform aperture and the anterior teeth of maxilla. The screws may have a size between 2 mm and 8 mm. A step of cutting the bone surface with a drill bur may first be performed before screwing the metal implant plate into the bone surface with screws. Specifically, first a drill bur is used to drill a hole with a diameter of about 1.7 mm and a depth of about 5 mm. Then, the screw is inserted. The screw may have a 2 mm diameter and a length between 5-8 mm. It is understood that the dimensions described herein are provided as non-limiting examples and that other suitable dimensions of the hole or the screw may be applied to the method described herein.

The method 100 may then include a step of imaging the jaw bone of the patient again to confirm that there is no penetration of the screws into the nasal cavity and no contact between the screw and the root of the implant. A step of suturing may then be performed in the method 100 to close the site of the patient. The step of suturing may be performed using 6-0 Vicryl periosteal sutures and 5-0 silk gingival sutures.

Example 1

Methods

Figure 2A:
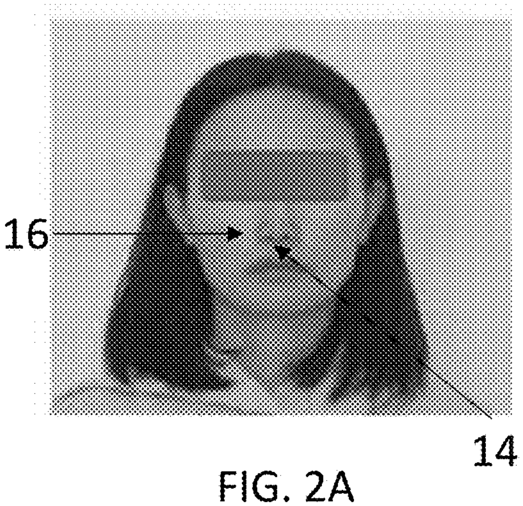
FIG. 2A a is a front view of a patient's face before the surgical method of FIG. 1 is performed on the patient.
Figure 2B:
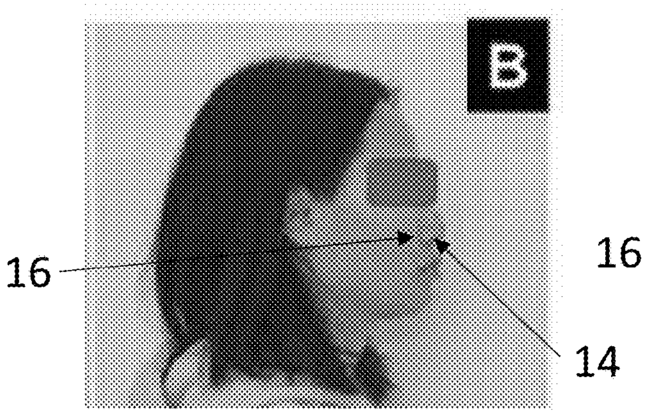
FIG. 2B is a lateral view of the patient's face before the surgical method of FIG. 1 is performed on the patient.
Figure 2C:
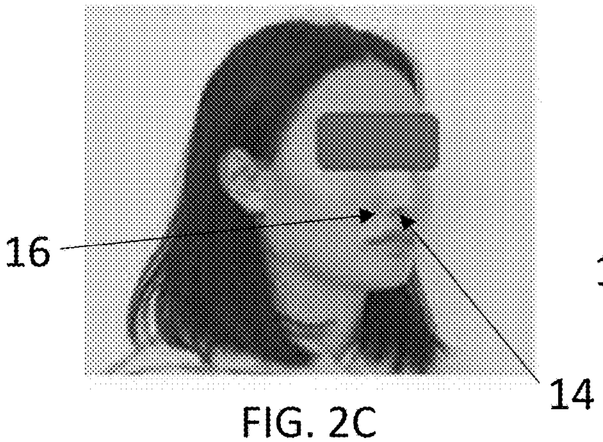
FIG. 2C is a perspective view of the patient's face before the surgical method of FIG. 1 is performed on the patient.

With reference to FIGS. 2A-C, a 26-year-old woman ("the patient") diagnosed with misaligned dentition, having good general nutrition and no significant medical and family history, showed strong depression of the midface, base of the nasal column 14, and base of the ala 16. Specifically, the nasolabial angle was 74°, which is narrower than the mean value of 87.86° for Asians and 109° for Caucasians. The Sn-Pog' to the upper lip of Legan-burstone soft tissue analysis was 6.5 mm, similar to the Japanese standard value of 6.5 mm, yet higher than the Caucasian standard value of 3.0 mm, suggesting a diagnosis of protrusion of the mouth (see Table 1, below).

TABLE 1

Feature Measurements Before and After Surgery.

| Analysis Items | Standard Values Mean (Asian) | Standard Values Mean (Caucasian) | Before Surgery | After Surgery |
|---|---|---|---|---|
| Facial convexity (Glabella-Sn-Pog) (°) | 7.6 | 14.79 | 3.3 | 7.6 |
| Nasolabial Angle (°) | 87.86 | 109 | 74 | 90.2 |
| THL (°) | | | 50 | 73 |
| Sn-Pog to Upper Lip (mm) | 6.5 | 3 | 6.5 | 4.7 |
| Hard Point A to Soft Sn (mm) | | | 10.5 | 14.5 |
| Hard Point A to Nasal Apex (Pronasale) (mm) | | | 25.8 | 29.1 |
| N-Pog Line to Nasal Apex (Pronasale) (mm) | | | 24.8 | 26.1 |

Figure 4:
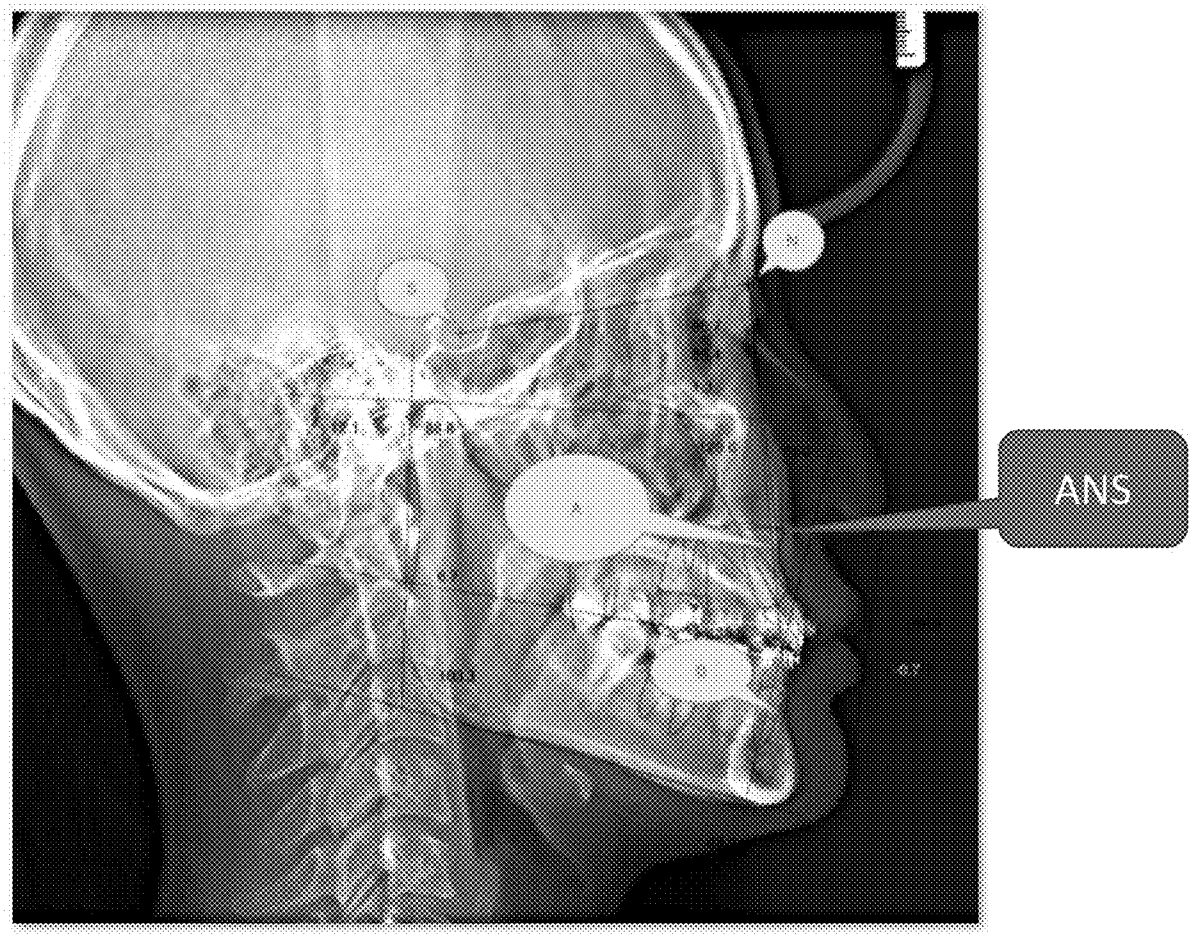
FIG. 4 is a lateral X-ray image of the patient's head before the surgical method of FIG. 1 is performed on the patient.

As depicted in FIG. 4, Tweed's analysis showed that the SNA angle (the angle between the sella/nasion plane and the nasion/A plane), the SNB angle (the angle between the sella/nasion plane and the nasion/B plane), and ANB angle (the relative position of the maxilla to the mandible, calculated by SNA angle−SNB angle) were 86.7°, 85.4°, and 1.3°, respectively, indicating a tendency toward mandibular protraction. There was a tendency for skeletal class III with mesofacial recessive growth, and the teeth presented with Angle class I. Therefore, the method disclosed herein was recommended to treat midface retraction of the patient.

Preoperatively, computed tomography (CT) imaging (Ray Japan α-Edge power, Tokyo, Japan) was performed on the patient's jaw bone. Thereafter, the jaw bone model was made using a three-dimensional printer (Form2, Form labs Inc., Kyoto, Japan), and the metal implant plate (Styker, MI, USA), which served as a frame, was bent to match the bone surface form of the jaw bone model. The plate used for the surgery was made of titanium, and the thickness was 2 mm for durability. Considering the restrictions regarding both the location of screwing and the strength of fixing, a plate with two holes was used. Surgical simulation and simple bending of the implant metal plates were performed using a jaw bone model. Patient consent was obtained for the off-label use of metal plates.

Figure 5A:
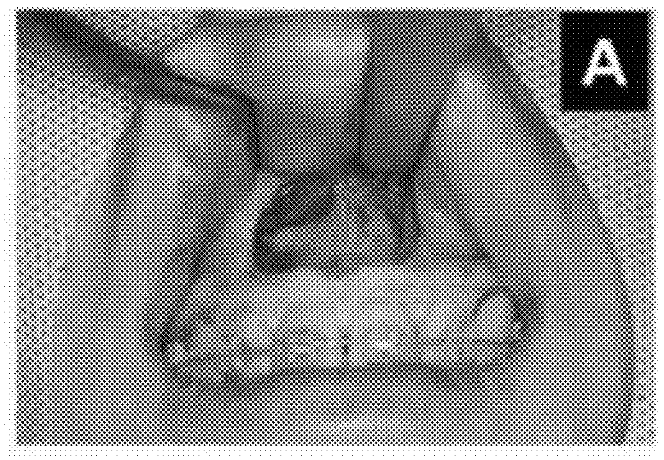
FIG. 5A is an image of a site of the patient after being dissected according to the method of FIG. 1.
Figure 5B:
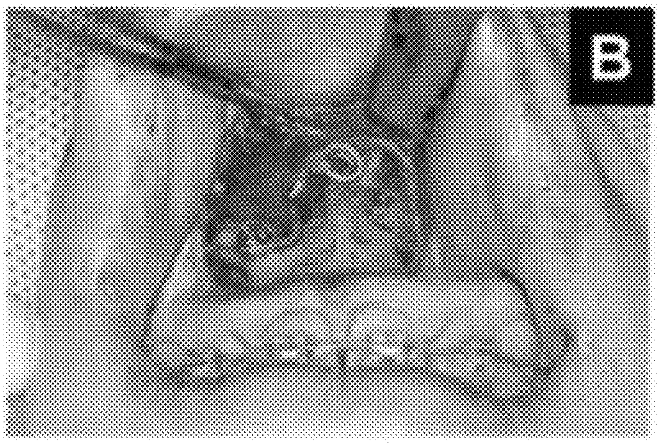
FIG. 5B is an image of the site of the patient after the metal implant plate is fixed to a bone surface of the patient at the site, according to the method of FIG. 1.
Figure 5C:
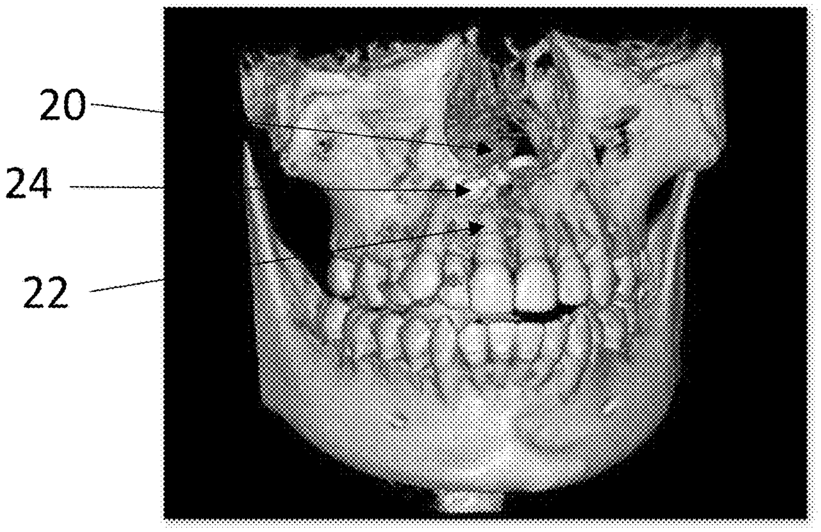
FIG. 5C is an image of a jaw bone model of the patient having the metal implant plate attached to a surface of the jaw bone model of the patient.
Figure 5D:
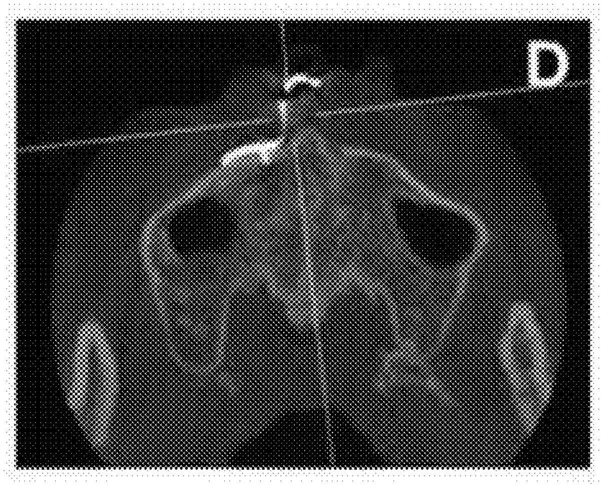
FIG. 5D is a computed tomography image of the site of the patient after the metal implant plate has been fixed to the bone surface, according to the method of FIG.
Figure 5E:
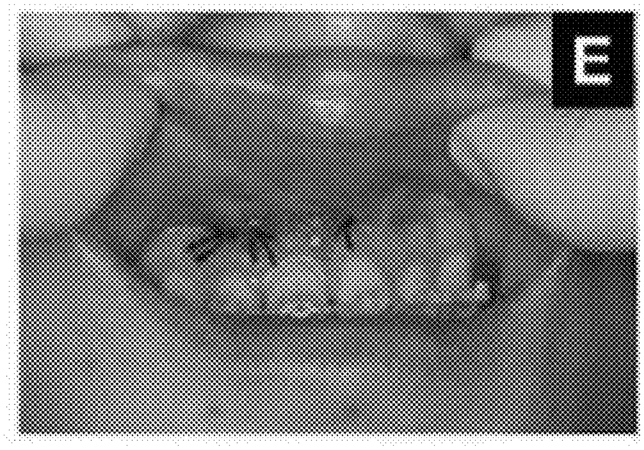
FIG. 5E is an image of the site of the patient after the site has been sutured closed.

On the day of surgery, the patient had a good general condition and no nasal symptoms. Surgery was performed under local anesthesia using six doses of Aura Injection Dental Cartridge (Showa Pharmaceutical Co., Ltd. Aichi, Japan), with 1.8 mL per dose. After incision and gingival mucosal dissection from the left and right side of the gum-buccal junction of the maxilla using blade no. 15, condition of the bone was confirmed to be good (FIG. 5A). Morphological modifications of the metal implant plate and modified bending were performed. For example, the metal implant plate is initially straight but may be bent to fit the bone, as seen in FIG. 5B. It was confirmed that the nasolabial angle was sufficiently increased by viewing the forward movement of the soft tissue Sn point from the outside of the mouth. Thereafter, the metal implant plate was bent again to match the bone surface, as a final adjustment. After metal implant plate bending, the bone was cut with a drill bur as described above and two screws with a diameter of 2.0 mm and a length of 5.0 mm were embedded, and the metal implant plate was fixed to the bone surface (FIG. 5B). The position of the screw was set between the lower edge of the piriform aperture 20 and the anterior teeth of maxilla 22, which is the safest and secures the depth of the bone. For example, the position of the screw was set to area 24. CT was performed immediately after the screws were embedded into the bone surface, which confirmed that there was no penetration of the screws into the nasal cavity and no contact between the screw and the root of the metal implant plate (FIGS. 5C and 5D). Suturing was performed using 6-0 Vicryl periosteal sutures and 5-0 silk gingival sutures (FIG. 5E). Antibiotics and analgesics were prescribed, and suture removal was done after two weeks. The clinical course was uneventful, with no infection of the wound. The requirements of the Helsinki Declaration were observed. The patient provided informed consent for all surgical procedures.

Results

Figure 3A:
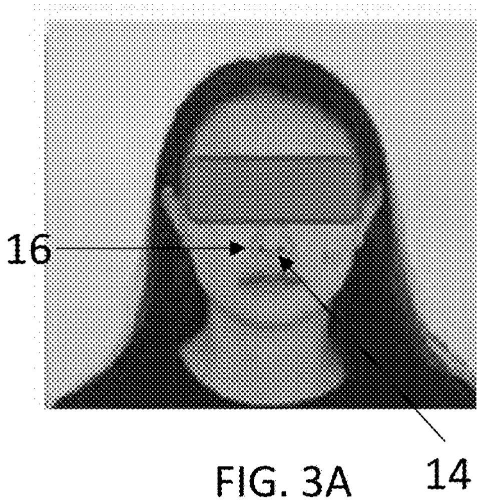
FIG. 3A is a front view of the patient's face after the surgical method of FIG. 1 is performed on the patient.
Figure 3B:
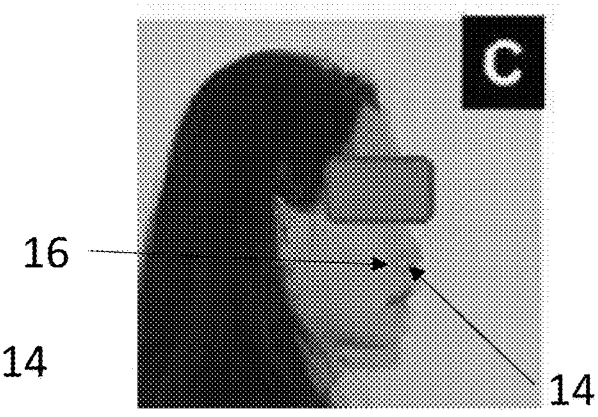
FIG. 3B is a lateral view of the patient's face after the surgical method of FIG. 1 is performed on the patient.
Figure 3C:
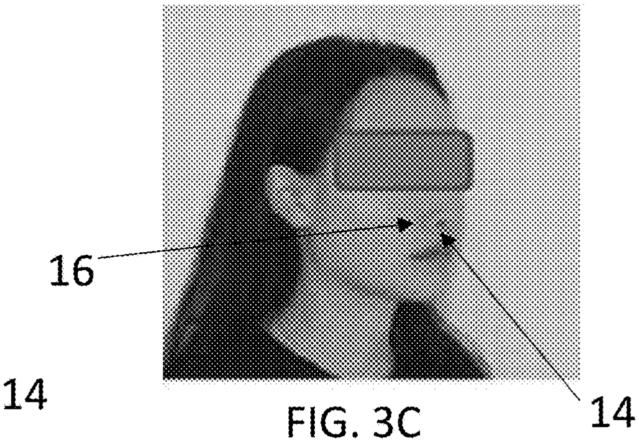
FIG. 3C is a perspective view of the patient's face after the surgical method of FIG. 1 is performed on the patient.
Figure 6A:
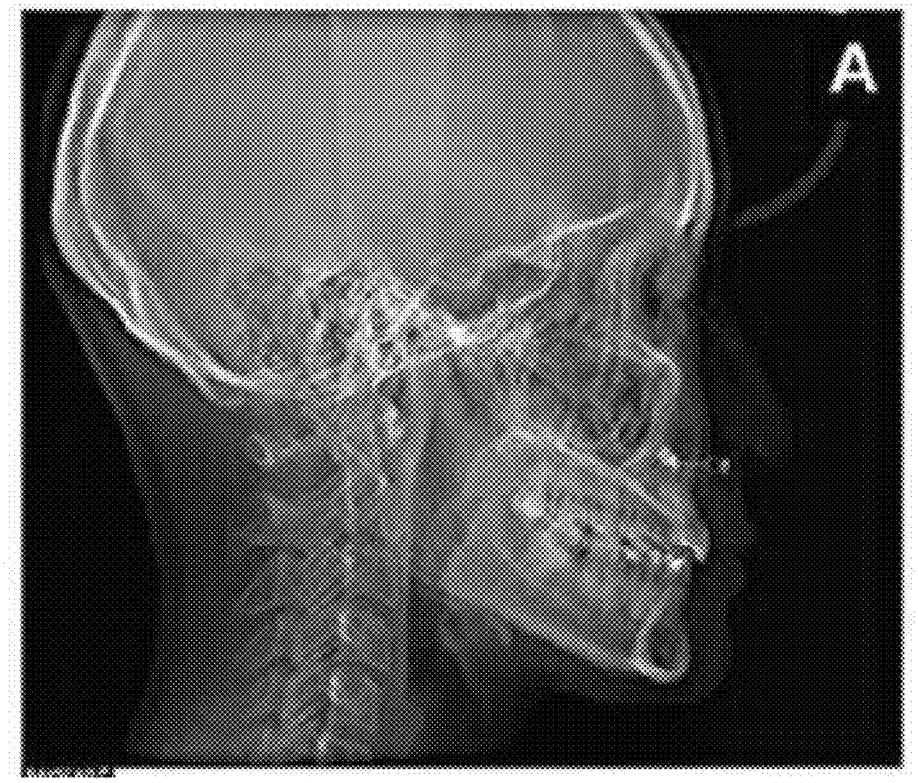
FIG. 6A is a lateral X-ray image of the patient's head after the surgical method of FIG. 1 is performed on the patient.
Figure 6B:
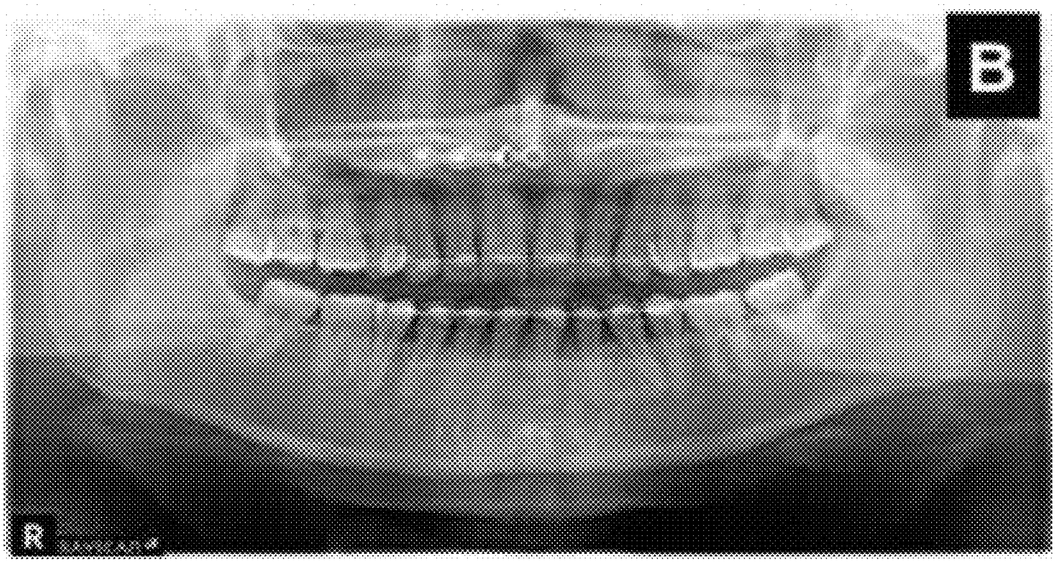
FIG. 6B is a panoramic X-ray image of the patient's mouth after the surgical method of FIG. 1 is performed on the patient.

The comparison of the pre-surgery facial photographs depicted in FIGS. 2A-C and the post-surgery facial photographs depicted in FIGS. 3A-C show an increase in the nasolabial angle and anterior migration of the soft tissue Sn point (also see Table 1). Moreover, symptoms of discomfort, such as pulling of the nose after prosthesis insertion were not identified. The swelling at the operative site also receded in approximately two weeks. There were no abnormal findings on skull five months after surgery in a panoramic and lateral facial X-ray, as depicted in FIGS. 6A-B.

Changes in lateral facial features and positional changes in the nasal apex (i.e., pronasale) before surgery and five months after surgery are shown in Table 1 and the comparison of FIGS. 2A-C and FIGS. 3A-C. The following changes were observed on soft tissue analysis of the lateral facies: facial convexity from 3.3° to 7.6°; nasolabial angle from 74° to 90.2°; true horizontal line from 50° to 73°; and Sn-Pog' to upper lip from 6.5 mm to 4.7 mm. Serial movements indicated that surgery improved the aesthetics of the lateral view of the face. When the positional changes of the nasal apex (i.e., pronasale) were examined on cephalometric radiographs, hard point A to soft tissue Sn changed from 10.5 mm to 14.5 mm, hard point A to nasal apex (i.e., pronasale) from 25.8 mm to 29.1 mm, and hard N-Pog' line to nasal apex (i.e., pronasale) from 24.8 mm to 26.1 mm. therefore, the nasal apex shifted anteriorly.

Discussion

This case depicted a clear preoperative line-to-mouth positional relationship between the lip and E-line. However, there was a feeling of midface retraction and protrusion of the mouth, owing to the posterior location of the soft tissue Sn. Therefore, to achieve a better aesthetic outcome for the patient, repositioning the soft tissue Sn anteriorly using the method described herein was performed, resulting in changes in the lateral view of the face.

Facial convexity is a key indicator of the stereoscopic appearance of the face. Asian people, for example, often find stereoscopic faces more aesthetically pleasing, with a mean angle of 7.6° for Asians and 14.79° for Caucasians. Referring again to Table 1, above, the facial convexity angle of the patient was 3.3° before operation and 7.6° after the operation. Therefore, a better stereoacuity of the patient's face could be achieved. Another key indicator of an aesthetically pleasing face is the nasolabial angle, which is ideally 109° and 105° for Caucasian women and men, respectively. The nasolabial angle of the female patient before operation was 74° and 90.2° after the operation, suggesting that the ideal nasolabial angle was obtained by the surgery. For midface retraction, the anterior positioning of the soft tissue Sn-point may improve the nasolabial angle while reducing the amount of tooth movement during orthodontic treatment. The angle of the upper white lip that forms the nasolabial angle between 79° and 85° is considered ideal for the true horizontal line when the patient is standing, wherein the soft tissue Sn-point is used as the origin. In the present example, the preoperative true horizontal line was 50°, and it reached 73° after surgery, which was a significant improvement despite the inability to reach the ideal value. The Sn-Pog' to the upper lip of Legan-burstone soft tissue analyses are key indicators of the sensation of protrusion of the oral cavity. For the Asian people, the tendency of protrusion is common. The Sn-Pog' to the upper lip is 6.5 mm in Asian women and 6.3 mm in men, while for Caucasians, the mean value is at 3.0 mm. The patient's preoperative measurement was at 6.5 mm, and changed to 4.7 mm after the operation, suggesting that the feeling of mouth protrusion was relieved. It can be inferred that the changes in the above parameters were due to the forward shift of the Sn point using the method described herein.

The plates and screws used in the surgery were made of titanium. Dental implants are a typical example of titanium used in biotherapy. Bone resorption does not occur unless it is under special circumstances, such as bacterial infection. In addition, when the titanium plate for fracture treatment or orthodontic treatment is removed at a later date, it was observed that bones were formed on the titanium plate. Since the plate used for surgery has a small contact area with the bone surface, it seems that blood flow was not impaired and therefore, bone resorption was unlikely to occur. Although the treatment was performed to reduce midface retraction, it was confirmed that the nasal apex was simultaneously shifted forward upon comparison of the cephalometric radiographs. The N-Pog' line was noted to change 2.5 mm anteriorly before and after surgery. This made E-line look more appealing.

Generally, according to the method disclosed herein, a nasolabial angle may be widened and the Sn moves anteriorly. By pushing from behind with a titanium plate, the Sn may move forward. This produces a three-dimensional effect on the midface, as the nasolabial angle is widened and the protruding mouth is reduced. In the vacant space, autologous tissue proliferates. This guarantees blood flow and so on while maintaining the structure of the metal implant plate. In addition, the ANS point in FIG. 4 appears to move forward with this titanium plate.

Although the above disclosure has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments. In addition, while a particular feature may have been described above with respect to only one or more of several illustrated embodiments, such feature may be combined with one or more other features of the other embodiments, as may be desired and advantageous for any given or particular application.

What is claimed is:

1. A surgical method for changing a nasolabial angle of a patient, the method including the steps of:

forming a metal implant plate using a jaw bone model of the patient;

dissecting a site on the patient for implantation of the metal implant plate;

bending the metal implant plate to match a bone surface of a jaw bone of the patient at the site;

fixing the metal implant plate to the bone surface to increase the nasolabial angle of the patient.

2. The surgical method according to claim 1, further comprising a step of applying local anesthesia to the site of the patient before dissecting the site.

3. The surgical method according to claim 1, further comprising a step of confirming that there is no penetration of two screws into a nasal cavity of the patient and that there is no contact between the two screws and a root of the metal implant plate.

4. The surgical method according to claim 1, further comprising a step of suturing the site closed.

5. The surgical method according to claim 1, wherein the step of forming the metal implant plate includes the steps of:

imaging the jaw bone of the patient;

forming the jaw bone model of the patient; and bending the metal implant plate to match a model jaw bone surface of the jaw bone model.

6. The surgical method according to claim 5, wherein the step of imaging the jaw bone of the patient includes imaging with computed tomography (CT) imaging.

7. The surgical method according to claim 5, wherein the step of forming the jaw bone model of the patient includes forming the jaw bone model by three-dimensional printing.

8. The surgical method according to claim 1, wherein the step of dissecting the site includes dissecting a gingiva mucosa of the patient from a gum-buccal junction of a maxilla of the patient.

9. The surgical method according to claim 1, wherein the fixing the metal implant plate to the bone surface includes the steps of:

cutting the bone surface; and embedding two screws into the bone surface.

10. The surgical method according to claim 9, wherein the step of cutting the bone surface includes cutting the bone surface with a drill bur.

11. The surgical method according to claim 9, wherein the two screws each have a diameter of 2.0 mm and a length of 5.0 mm.

12. The surgical method according to claim 9, wherein the step of embedding the two screws into the bone surface includes screwing each of the two screws into the bone surface between a lower edge of a piriform aperture and an anterior teeth of a maxilla of the patient.

* * * * *